US006511450B1

(12) United States Patent
Bauermeister

(10) Patent No.: US 6,511,450 B1
(45) Date of Patent: Jan. 28, 2003

(54) DEVICE FOR THE EXTENSION OF THE SPINE

(76) Inventor: Wolfgang Bauermeister, Unnutztrasse 17 a. D-81825, Munich (DE)

( * ) Notice: Subject to any disclaimer, the term of this patent is extended or adjusted under 35 U.S.C. 154(b) by 0 days.

(21) Appl. No.: 09/312,106

(22) Filed: May 14, 1999

(30) Foreign Application Priority Data

May 17, 1998 (DE) ........................................ 198 21 962

(51) Int. Cl.[7] .................................................. A61F 5/00

(52) U.S. Cl. ........................................... 602/33; 602/32

(58) Field of Search .......................... 602/33, 34, 36.9, 602/835, 32, 37; 482/69; 606/240, 245; 601/23, 24

(56) References Cited

U.S. PATENT DOCUMENTS

| | | | | |
|---|---|---|---|---|
| 2,831,482 A | * 4/1958 | Cobb | .......................... | 602/33 |
| 3,817,512 A | * 6/1974 | Torrey | ........................ | 269/328 |
| 3,856,003 A | * 12/1974 | Pfluger | ........................ | 602/33 |
| 4,253,207 A | * 3/1981 | Marcyan | ...................... | 601/24 |
| 4,405,128 A | * 9/1983 | McLaughlin et al. | ......... | 482/97 |
| 4,454,870 A | * 6/1984 | Schwentker | ................. | 602/33 |
| 4,641,637 A | * 2/1987 | Rosen | ......................... | 128/75 |
| 5,352,185 A | * 10/1994 | Blauth et al. | ................. | 601/32 |
| 5,478,307 A | * 12/1995 | Wang | .......................... | 602/32 |
| 5,567,202 A | * 10/1996 | Hager | ........................ | 482/131 |
| 5,681,272 A | * 10/1997 | Lee | ............................. | 602/32 |
| 5,916,189 A | * 6/1999 | Sullenperger et al. | ........ | 602/36 |

FOREIGN PATENT DOCUMENTS

| | | | | |
|---|---|---|---|---|
| CA | 770404 | * 10/1967 | .................. | 128/28 |
| DE | 33 02 395 | 7/1984 | | |
| EP | 334 274 | 9/1989 | | |

OTHER PUBLICATIONS

"Lossing Necktrac with Digital Electronic Load Sensor Model 6911"; (4 p. ); Pub. 1994; Lossing Orthopedic, Inc.
"Cervical Traction with Digital Sensor"; (2 p. ); Undated; Lossing Orthopedic, Inc.
"Backtrac (90/90 Traction) ® Classic Clinic Package Model 491"; (4 p.); Pub. 1994; Lossing Orthopedic, Inc.
"Lossing 90/90 Distrac Lumbar Traction/Distraction Instruction Manual Model 4911"; (8p.); Pub. 1995; Lossing Orthopedic, Inc.

* cited by examiner

*Primary Examiner*—Justine R. Yu
(74) *Attorney, Agent, or Firm*—Kilpatrick Stockton LLP

(57) ABSTRACT

The invention proposes a device for spinal column extension (1), in which the carrier part (4) bearing the attachment point (40) or the attachment element (45) for the transfer part (451) for the traction to be applied to the area of the spinal column of the patient (10) to be treated is pivotably mounted (70) relative to the base part (2). Thereby it is possible for the device (1) to be used more simply for cervical spinal column extension in various areas and even additionally for lumbar spinal column extension.

4 Claims, 4 Drawing Sheets

DEVICE FOR THE EXTENSION OF THE SPINE

FIELD OF THE INVENTION

Background of the Invention

The invention pertains to a device for the extension of the spine for spinal column extension with a base part and a carrier part affixed thereto, on the upper section of which is located an attachment element for the transfer part for the traction acting upon the body to be treated, while the height of the attachment element is adjustable in relation to the base part.

Such a device is known from the prospectus "LOSSING® Necktrac® Digital Electronic Load Sensor (Model 6911)" from 1994 with the number "OR360" of Lossing Orthopedic, Inc., Minneapolis, Minn., U.S.A.

"base part" is understood to be the part of the device usually lying on the floor, or possibly also on the slab of a treatment table, on which the body of the patient to be treated rests directly or indirectly, and which as a rule is held securely in place by the weight of the patient's body.

The carrier part is a part projecting up therefrom, on which, in the aforesaid state of the art, the neck loop is affixed by a cable to an overhead attachment point. The neck loop is placed around the head of the patient and the head of the patient is drawn toward the attachment element by shortening the cable with the usual means (direct traction, pulley block or the like) and the cervical spinal column is extended thereby. As a rule, the patient is so positioned that his head is directed toward the carrier part and the back of the patient is toward the base part.

Since, depending upon the problem to be treated, different parts of the cervical spinal column are to be extended, the height of the attachment element in relation to the base part is adjustable, whereby the connecting line from the loop to the attachment point is variable. Here it is disadvantageous that the patient must then slide on the base part in order to reach the desired tension angle. In the case of the cited device, it is also disadvantageous that other parts of the spinal column, e.g., the pelvic area, cannot be treated therewith, so that an additional device is required.

BRIEF SUMMARY OF THE INVENTION

Accordingly, the invention specifies a device of the cited type, which is simpler yet more versatile to employ than the devices known heretofore for spinal column extension. This is achieved according to the invention in that the carrier part is articulately joined to the base part. The solution according to the invention has the following specific advantages:

With the articulation of the carrier part, the height and separation adjustments between the head of the patient and the attachment element can be simultaneously made when the carrier part is pivoted away behind the head of the patient (as a rule in the plane of symmetry of the entire device). Then it is no longer necessary for the body of the patient to be displaced on the base part, which routinely led to difficulties due to the displacement of the intervening mats and similar problems when the device was employed.

When, on the other hand, the carrier part is pivoted in the direction of the base part, then with appropriate positioning the attachment element can be swung over the middle of the body of the patient and then a loin belt can be affixed to the attachment element, which makes it possible to stretch the lumbar spinal column, as it is described, e.g., in the prospectus "Backtrac (90/90) Traction® Classic Clinic Package Model 491) of the aforementioned Lossing Orthopedic, Inc., 1994, No. OR94-071.

The device according to the invention can therefore fulfill the functions of two devices of the state of the art, which obviously results in appreciable cost savings and an easier transportability of the entire equipment.

Preferably, the carrier part can be locked in various pivoted positions.

It is entirely feasible that the pivoting movement of the carrier part strikes a stop in two end positions, which represent an ordinary position for extension of the cervical spinal column and an ordinary position for extension of the lumbar spinal column. It is decidedly more advantageous, however, when the carrier part can be simply arrested at various pivoting angles and is releasable from this arrestability, while the settings are preferably adjustable in 15° steps. Ideally, the carrier part is pivotable from the vertical to 55° in the base part/patient direction for the lumbar spinal column extension and in the other direction pivotable from the vertical by 60° from the base part/patient for the cervical spinal column extension.

The pivoting line of the carrier part is preferably in a vertical plane.

When a lateral pivotability is also imaginable, a pivoting in the plane of the longitudinal axis of the body of the patient is meaningful and sufficient as a rule.

Preferably, the carrier part is designed as a U-bend open at the bottom, ideally a U-shaped bend of pipe.

Here the distance between the arms preferably and approximately corresponds with the width of the shoulders of the patient. The carrier part can then be simply swung over the patient without the patient colliding therewith. Furthermore, the patient can, with suitable attachment to the ends of the arms, disengage and reengage the locking mechanisms and change the angle of inclination of the carrier part without changing his own position.

Preferably, the base part is designed as a U-shaped bend open toward the carrier part, ideally a U-shaped bend of pipe, the ends of the arms of which are articulately joined to the ends of the arms of the carrier part.

This results in a device which is overall very easy and simple to transport.

In a practical sense, the pivotability of the two U-shaped pipe bends is so designed that in a special position they can be folded together, so that the entire device is completely flat and can be easily transported accordingly.

BRIEF DESCRIPTION OF THE DRAWING

The invention is described in greater detail below with references to the appended drawings, to which, because of their great clarity and lucidity, specific attention is invited in respect to the disclosure. These depict.

DETAILED DESCRIPTION OF PREFERRED EMBODIMENT

Figure 1:
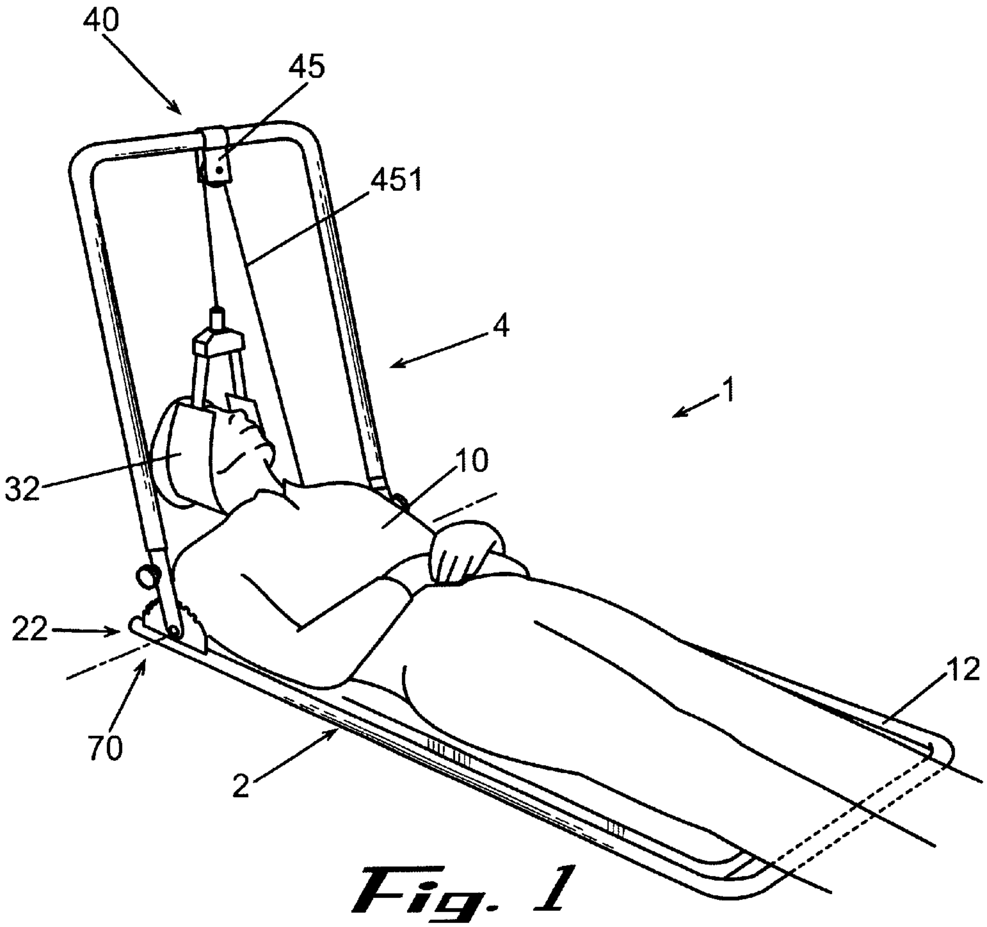
FIG. 1: The device according to the invention, with a patient, in a first position, with the carrier part pivoted slightly to the rear for cervical spinal column extension in the lower area.
Figure 1A:
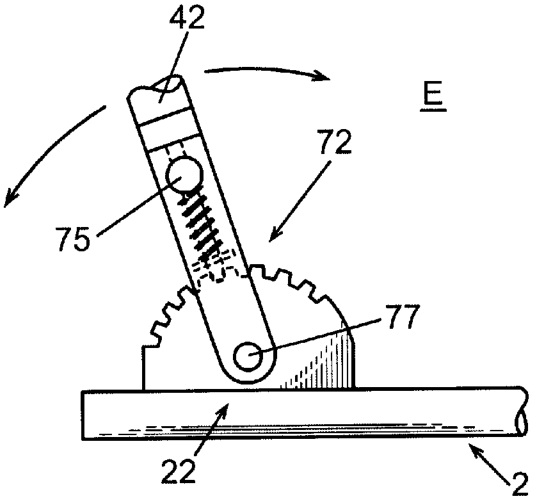
FIG. 1*a*: A possible and practical locked direction in greater detail.

FIG. 1 shows the device (1), with a patient (10), in a first position for extension of the cervical spinal column. The base part (2) lies on the floor. In the base part there is a mat (12), which is laid into the base part and, as a result of the weight of the patient, prevents slippage of the base part (2) in relation to the patient (10), more or less due to the tension of the cable (451).

The base part (2) is, as shown, designed as a U open toward the head of the patient (10) and made of a (light metal) pipe with a diameter of 25 mm, an arm length of 1200 mm (1115 mm to the pivot axis) and a width across both arms of 560 mm.

The end (22) and the corresponding other end of the arms bear a locking mechanism (70) in the form of an entity like a cogwheel, which is engaged by a locking rod displaceable against spring action. The locking rod is borne in the endpieces (42) of the arms of the carrier part (4) and can be released from the locking teeth with the help of a respective button (75), whereupon the carrier part (4) can be pivoted on the bolt (77) relative to the base part (2). In this embodiment the pivoting takes place in the plane (E) of the cogwheels, while each of the remaining steps represent 15°. Here the length of the arms of the carrier part (4) is 940 mm to the arm bolt and the width is again 560 mm.

Mounted in the apex (40) inside of the carrier part (4), i.e., in the middle of the transverse pipe connecting the arms, is an attachment element (45) (e.g., in the manner of a pipe clamp), to which attachment element a transfer part (451), here a cable, is attached, which bears the carrier loop for the body part to be treated, in this case the neck.

The cable can be equipped in a known manner with a Bowden control and, optionally, an element for monitoring or adjusting the tension, which is not further shown here.

Figure 2:
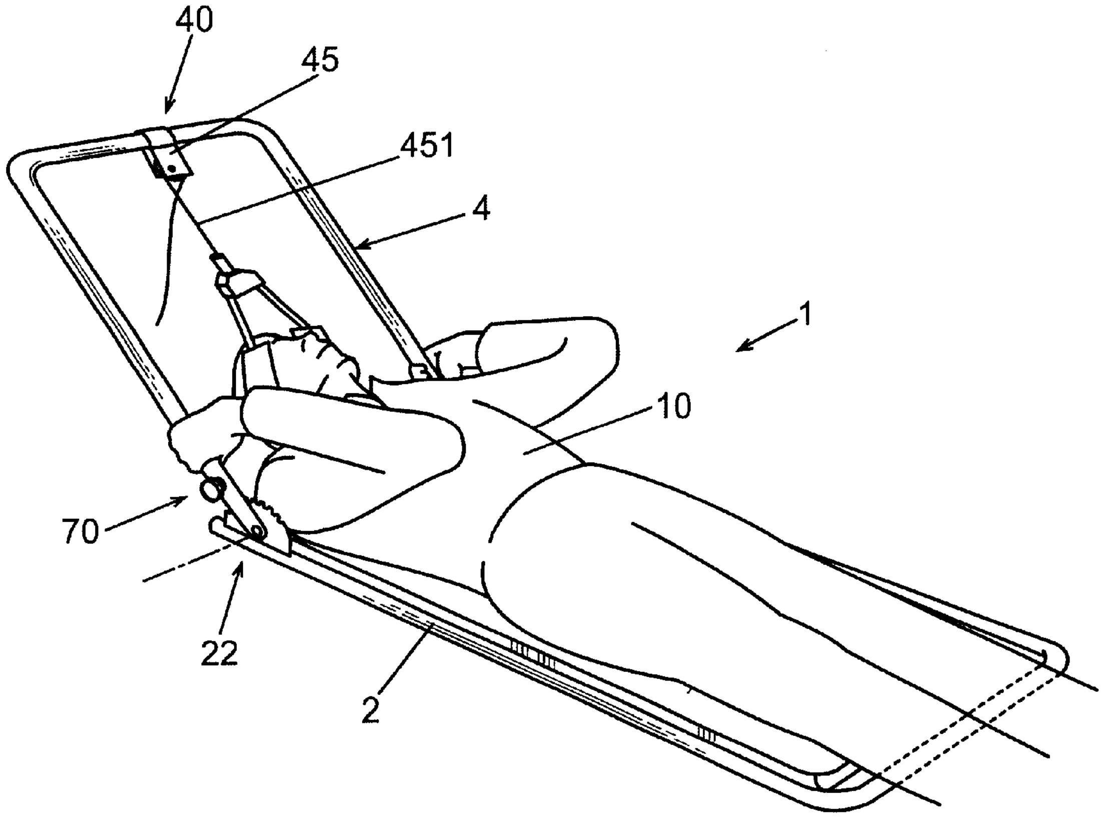
FIG. 2: The device in FIG. 1, with a patient, with a position of the carrier part pivoted farther away from the patient for extension of the cervical spinal column in the upper area.

The device is shown in FIG. 2 in another angular setting of the carrier part (4) relative to the base part (2). Identical reference symbols indicate identical or similar parts. As shown, the person (10) to be treated can personally disengage the locking mechanism by pulling on the button (75) and move the carrier part (4) into the desired angular position and again lock it there. The device is, therefore, also very good for self treatment following applicable instruction. With the change of the angular setting, the height of the attachment element (45) relative to the base part (2) has clearly also changed.

Figure 3:
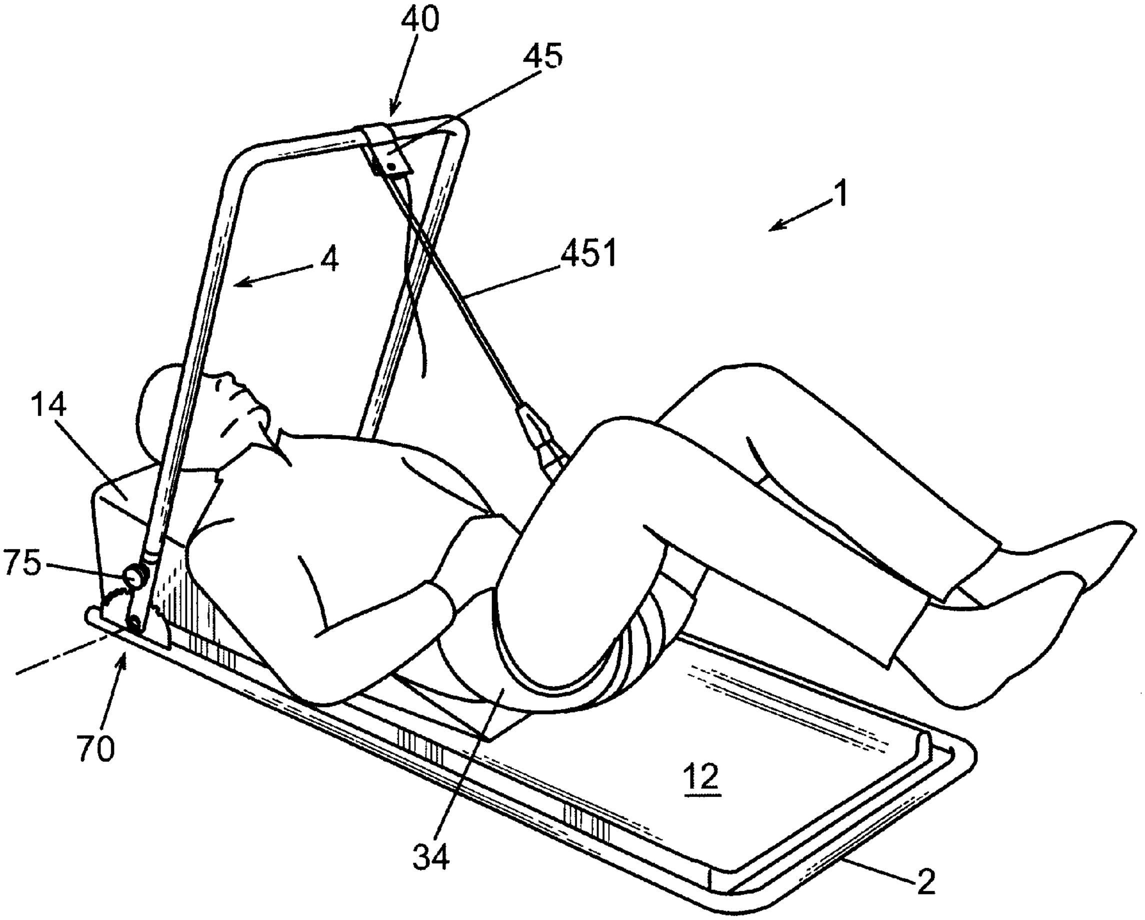
FIG. 3: The device, with a patient, in a third position, in which the bend of the carrier part is pivoted above the patient into a position above the base part for extension of the lumbar spinal column.

FIG. 3 shows the device (1) in another setting, in which the carrier part (4) is pivoted relative to the base part (2) past the vertical (90°) position out over the base part (2). The patient (10) lies on the aforementioned mat (12) and an additional wedge (14). In order to realize the essential inclination of the spinal column for the best possible effect, the legs are bent and rest on a (undepicted, however, cf. FIG. 4) support device, e.g., a stool or platform. Instead of the loop (32) for the CSC (cervical spinal column) extension, the transfer part (451) is here affixed to a belt (34) for the LSC (lumbar spinal column) extension. The overall pivot angle is approximately 150°.

Figure 4:
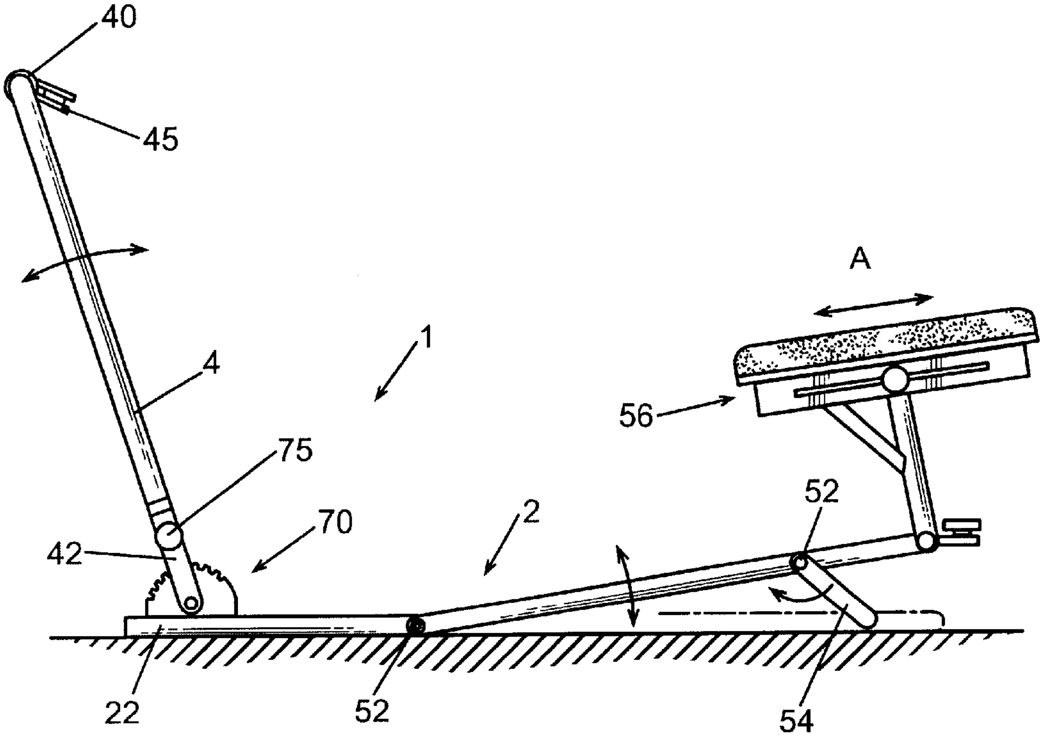
FIG. 4: A schematic side view of the device with additional adjustment possibilities and supplemental mechanisms.

FIG. 4 shows in side view a device (1) essentially like that in FIGS. 1–3, albeit without the person (10) to be treated. Here possible additional and advantageous adjustment possibilities are shown. The frame of the base part (2) can here be additionally folded at a hinge (52), so that the foot area and/or the head area can be raised. The elevated foot area can be supported by additional fittings (54) articulately affixed to the base part (2). Comparable fittings (not shown here) are provided for the head area, so that, e.g., with appropriate securing of the mat (12) (cf. FIGS. 1–3), the upper body or the head of the person to be treated can be raised without using the wedge (14) (FIG. 3). The elevation of the feet cited above as advantageous for the LSC extension is here made possible by a platform (56) affixed to the end of the frame of the base part (2), which is optionally adjustable for height and, as indicated, adjustable in direction (A) and optionally also horizontally adjustable by the additional fittings in relation to the tilting of the frame part.

Figure 5:
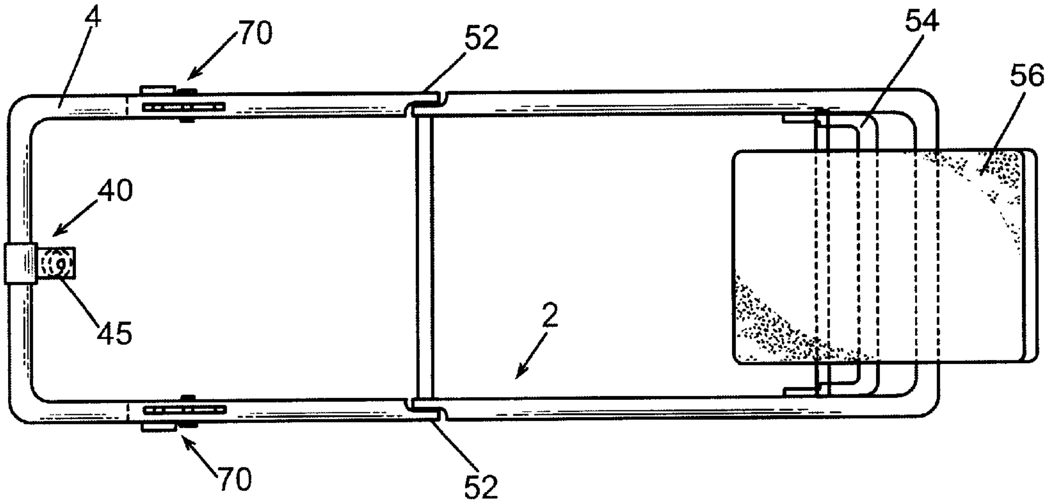
FIG. 5: The device in FIG. 4 in top view, schematic.

FIG. 5 depicts, in the interest of clarity, another view of the device in FIG. 4, wherein identical reference symbols indicate identical or similar parts.

The device (1) has yet another setting (not illustrated), in which the carrier part (4) and the base part (2) can be folded together (0°-setting), so that the device already producible with a very light weight can also be space-savingly stored.

What is claimed is:

1. A device for spinal column extension, comprising:

a base part (2) having a lengthwise extent on which a body to be treated may recline, and a carrier part (4) attached to the base part;

an attachment element (45) located on an upper section of the carrier part (4) to receive a transfer part (451) for applying traction to a body to be treated while reclining on the base part; and the carrier part (4) being pivotally joined (70) to the base part (2) so as to selectably and arrestably vary the angular setting of the carrier part in a first range of angular positions less than vertical relative to the lengthwise extent of the base part, and in a second range of angular positions greater than the vertical relative to the lengthwise extent of the base part, whereby in the first plurality of positions the attachment element is located relative to the base part (2) for applying traction for extension of the lumbar spinal column of a body on the base part in response to a selected angular setting in said first range of angular positions, and in the second range of angular positions the attachment element is located relative to the base part for applying traction for extension of the cervical spinal column of the body in response to a selected angular setting in said second range of angular positions.

2. Device according to claim 1 wherein the carrier part (4) joins to the base part (2) along a pivot line that lies in a vertical plane.

3. Device according to claim 1 wherein the carrier part (4) is designed as a U-shape bend (4), open at the bottom and having an apex (40) in which the attachment element (45) is located.

4. Device according to claim 2, wherein the base part (2) is designed as a U-shaped bend (2) open toward the carrier part (4) and having legs (22) with ends that are articulately joined (70) to the ends of legs (42) of the carrier part (4).

* * * * *